(12) United States Patent
Noguchi et al.

(10) Patent No.: US 8,216,511 B2
(45) Date of Patent: Jul. 10, 2012

(54) SPECIMEN RACK AND SPECIMEN CARRIER SYSTEM

(75) Inventors: Kiyoteru Noguchi, Tokyo (JP); Hitoshi Ohtake, Hitachinaka (JP); Yoshimitsu Takagi, Hitachinaka (JP); Takuya Yamaguchi, Hitachinaka (JP); Yoshiaki Saito, Hitachinaka (JP); Yasuaki Takebe, Fujisawa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 376 days.

(21) Appl. No.: 12/128,728

(22) Filed: May 29, 2008

(65) Prior Publication Data

US 2008/0299007 A1 Dec. 4, 2008

(30) Foreign Application Priority Data

May 30, 2007 (JP) ................................ 2007-142775

(51) Int. Cl.
*B01L 3/00* (2006.01)
*G01N 21/00* (2006.01)
*G01N 21/75* (2006.01)
*B65D 85/00* (2006.01)
*G01N 1/16* (2006.01)
*G01N 31/00* (2006.01)
*G01N 33/00* (2006.01)
*G06F 7/00* (2006.01)

(52) U.S. Cl. .................... 422/65; 73/863.31; 73/864.91; 422/63; 422/64; 422/67; 422/68.1; 422/400; 700/225; 700/226; 206/459.5

(58) Field of Classification Search ........................ None
See application file for complete search history.

(56) References Cited

U.S. PATENT DOCUMENTS

| 4,701,754 | A | 10/1987 | Provonchee |
| 5,902,549 | A | 5/1999 | Mimura et al. |
| 6,141,602 | A * | 10/2000 | Igarashi et al. ............... 700/226 |
| 6,599,749 | B1 * | 7/2003 | Kodama et al. ................. 436/47 |
| 7,471,201 | B2 | 12/2008 | Ono |
| 2005/0002828 | A1 | 1/2005 | Gunji |
| 2005/0049799 | A1 | 3/2005 | Routburg |
| 2006/0000296 | A1 * | 1/2006 | Salter ......................... 73/863.01 |
| 2006/0039834 | A1 | 2/2006 | Itoh |
| 2007/0014693 | A1 * | 1/2007 | Kantrowitz et al. ............ 422/99 |
| 2008/0149656 | A1 * | 6/2008 | Yuyama et al. .................. 221/2 |
| 2008/0262651 | A1 * | 10/2008 | Luechinger et al. .......... 700/240 |

(Continued)

FOREIGN PATENT DOCUMENTS

CN        1168471 A       12/1997

(Continued)

OTHER PUBLICATIONS

Japanese Office Action issued May 18, 2011; Application No. 2008101088635.

(Continued)

*Primary Examiner* — In Suk Bullock
*Assistant Examiner* — Jennifer Wecker
(74) *Attorney, Agent, or Firm* — Antonelli, Terry, Stout & Kraus, LLP.

(57) ABSTRACT

A specimen rack and a specimen carrier system includes a luminous body disposed on a vicinity of a specimen container loading slot to notify, to an operator, information concerning an analyzing situation and condition of the specimen contained in the specimen container held by the specimen rack.

21 Claims, 5 Drawing Sheets

U.S. PATENT DOCUMENTS

2009/0129990 A1\* 5/2009 Kokawa et al. ............... 422/104

FOREIGN PATENT DOCUMENTS

| EP | 1 898 217 | 3/2003 |
| --- | --- | --- |
| JP | 53-047889 | 4/1978 |
| JP | 02-253854 | 10/1990 |
| JP | 11-083865 | 3/1999 |
| JP | 2001-124783 | 5/2001 |
| JP | 2005-009863 | 1/2005 |
| JP | 2005-067453 | 3/2005 |
| JP | 2006-030035 | 2/2006 |
| JP | 2006030035 A \* | 2/2006 |
| JP | A-2006-058219 | 3/2006 |
| JP | A-2006-178770 | 7/2006 |
| WO | WO 2007/024540 | 3/2007 |

OTHER PUBLICATIONS

Japanese Office Action issued Sep. 13, 2011; Application No. 2007-142775 and partial translation.

\* cited by examiner

| RACK ID | SPECIMEN ID | SPECIMEN CONTAINER LOADING SLOT POSITION | NOTIFICATION METHOD | |
|---|---|---|---|---|
| | | | LUMINOUS COLOR | LUMINOUS MODE |
| ⋮ | ⋮ | ⋮ | ⋮ | ⋮ |
| Rack_003 | Sample_123 | 1 | RED | TURN-ON |
| | Sample_124 | 2 | — | — |
| | Sample_125 | 3 | — | — |
| | Sample_126 | 4 | GREEN | BLINK |
| | Sample_127 | 5 | — | — |
| Rack_004 | Sample_128 | 1 | — | — |
| | Sample_129 | 2 | GREEN | BLINK |
| ⋮ | ⋮ | ⋮ | ⋮ | ⋮ |

VISUAL DIRECTION OF OPERATOR ial No. 2007-142775 filed on May 30, 2007,
SPECIMEN RACK AND SPECIMEN CARRIER SYSTEM

INCORPORATION BY REFERENCE

The present application claims priority from Japanese Application Serial No. 2007-142775 filed on May 30, 2007, the content of which is hereby incorporated by reference into this application.

BACKGROUND OF THE INVENTION

The present invention relates to a specimen rack and a specimen carrier system in which the specimen rack holds simultaneously a single or plurality of specimen containers containing specimens, for use in a pretreatment device and an analyzing device to treat (process) or analyze specimen samples such as bloods and urines, and the specimen carrier system is furnished inside or outside an apparatus which carries the specimen rack to the pretreatment device and analyzing device.

The pretreatment device and analyzing device have been grown in size with increase of test items and the number of specimens to perform a necessary treatment given to a specimen and to analyze it automatically for the specimen analysis. Meanwhile, to make a test work more efficient, the devices have been demanded for an enhancement of reliability, high throughput and low cost. For a purpose of enhancing a treatment performance, a specimen carrier system has been developed and commercially usable with use of coupling a plurality of devices, and the specimens are then carried by straddling the devices. A specimen rack has also been developed and commercially usable to be able to carry the plural specimens simultaneously.

The specimens held in the specimen rack are carried from an input portion of the specimen carrier system to the pretreatment device and analyzing device, and carried to an unloading position of the specimen carrier system, after the necessary treatment and analysis are completed. A pipette for sucking the specimen is sometimes clogged with a coagulation in the specimen on the treatment and analysis, depending on a quantity or condition of the specimen. In addition, an abnormality sometimes occurs such that a specimen fluid volume is short for the number of test items to analyze it. When the abnormality is detected, the devices judge a specimen condition from sensor information to immediately cease the analyzing operation for an abnormal specimen and to move to the analyzing operation for the next specimen. The abnormal specimen caused by the clogging and fluid volume shortage is applied again by the pretreatment and the like, and the abnormal specimen is repeatedly subject to the analysis.

In the case of a large size device, several tens to over hundreds specimen racks are carried by a carrier device, therefore, the total number of specimens on the carrier device could be several hundreds, depending on the number of specimens held by the specimen rack. In order to automatically and accurately associate each of such a great number specimens with analysis item and progress of analysis for the specimen and result of analysis, an ID such as a barcode is not only applied to a specimen container to read it reliably, but also applied to the specimen rack, as disclosed in JP-A-2-253854. Further, as disclosed in JP-A-11-83865, as an objective to realize a self-directive carry and analysis and to improve efficiency, a technique has been devised that the specimen rack has a communication unit and a readable and writable ID tag to exchange information between the devices. In this way, a high information processing performance is required to perform testing automatically and accurately for a number of test items and for a number of specimens. Therefore, an accessorius personal computer which the devices come with is mainly used for information processing in the case of the large size system.

SUMMARY OF THE INVENTION

However, after completing the successive treatment and analysis, it is necessary to compare an ID of a specimen to be classified and its position on an unloading position with displayed information on a monitor screen of an accessorius personal computer which the device come with and sheets printed separately so that the normally treated and analyzed specimen and the abnormally detected specimen caused by the clogging, fluid volume shortage and so forth are distinguished among the specimens aligned in the unloading position, for a purpose of classifying the specimens. A number of specimen containers and specimen racks that look alike are aligned in the unloading position. For this reason, in the case where the number of specimens is several hundreds, the work for judging and distinguishing and extracting the abnormal specimen while comparing it with the monitor screen and the printings of sheets is not only complicated and inefficient, but also possibly arouses an artificial mistake such as a switched specimen. For this reason, it is necessary to have a technique such that information is given to the specimen or specimen rack to transmit the information from the specimen or specimen rack, as required. However, the foregoing background techniques fail to provide a fundamental solution to the foregoing problem since they require an intervention of a certain information device such as a personal computer or mobile telephone to communicate with the device or the printed sheets for obtaining the information transmitted from the specimen or specimen rack.

An object of the invention is to provide a specimen rack and specimen carrier system capable of distinguishing and classifying conditions and positions of the target specimens without need to compare them with other information media by an operator by directly notifying outside of the analyzing situation and the specimen condition for each of the specimens aligned in the unloading position by using visual and intuitive means from the specimen rack.

In order to achieve the foregoing object, the present invention is constituted by the following constitutions.

A specimen rack that can hold simultaneously a single or plural specimen containers (normally, a test tube shape, but not limited to it), and have a notification unit that notifies, to outside, information concerning analysis situation and specimen condition for specimens each held on the specimen containers, and a communication unit that transmits and receives information necessary for a performance of the notification unit to and from outside. And, a specimen carrier system that carries the specimens to a pretreatment device that performs pretreatment for specimen analysis and to an analyzing device that analyzes the specimens, and have a communication unit that transmits and receives information to and from the specimen rack necessary for performing the notification unit.

A luminous body having a single or plural colors may be used for the notification unit of the specimen rack. The luminous body may be disposed on a top portion of the specimen rack or a portion above the top portion of the specimen rack. Alternatively, for a purpose of recognizing easily a correspondence between the luminous body and specimen, the luminous body may be disposed on a vicinity of a specimen container loading slot of the corresponding specimen, compared with a specimen container loading slot of a specimen which does not correspond to the specimen. By combining the colors of predetermined luminous body corresponding to the specimen, the amount of information notified to outside can be increased for the analysis situation and specimen condition for the specimen held on the single or plural specimen containers.

As a unit for receiving and supplying electric power necessary for the performance of the notification unit and communication unit in the specimen rack, a supply unit may be provided to supply electric power from the specimen carrier system to the specimen rack in a contact or non-contact manner. The specimen rack may have an accumulating unit to accumulate electric power supplied from the specimen carrier system or a battery charger. A supply unit may be provided at an input portion and/or the unloading position in the specimen carrier system to supply electric power to the specimen rack. In this case, a receiving unit is necessary for the specimen rack to receive electric power from the power supply unit provided in the input portion and/or the unloading position. In addition, in the case where the foregoing units are not relied to receive and supply the electric power necessary for performing the notification unit and communication unit of the specimen rack, the specimen rack should have an own power source to supply electric power for performing the notification unit and communication unit of the specimen rack.

As to the communication unit to communicate between the specimen rack and specimen carrier system, a transmission/reception unit for transmitting and receiving information necessary for the notification may be provided in the input portion and/or the unloading position by the contact or non-contact condition. A communication unit for transmitting and receiving the information to and from the communication unit provided in the input portion and/or the storage unit is provided in the specimen rack.

As a unit for storing information necessary for performing and controlling the notification unit provided in the specimen rack, the specimen rack is provided with a storage unit that temporarily stores all or part of information obtained from a communication with outside, and a storage unit that semi-permanently stores read-only information unnecessary for rewritten and erasure.

Particularly, the information, such as analysis situation and specimen condition for each of the specimens held on the specimen rack, that is temporarily stored in the storage unit of the specimen rack, can be erased by operating a button or a switch that is provided on the specimen rack or specimen carrier system or provided on a console or a operation screen which is a part of or is provided separately of the analyzing device or pretreatment device connected with the specimen carrier system.

Further, for the communication unit provided in the specimen rack to be able to operate as in the same way as it used to even after the input portion or the unloading position is removed from the main body of the specimen carrier system, the specimen rack or the input portion and/or the unloading position is provided with a communication unit that communicates by a wire or wireless system with the specimen carrier system or with a communication unit provided in a move destination of the input portion or unloading position. Further, the specimen rack or the input portion and/or the unloading position is provided with a unit for receiving electric power, by a wire or wireless system, necessary for performing and controlling the notification unit provided in the specimen rack from the main body of specimen carrier system or a power supply unit provided in the move destination of the input portion or unloading position after removed from the specimen carrier system.

With the foregoing constitution of the invention, the analyzing situation and the specimen condition for a number of specimens aligned in the unloading position are notified directly to outside by visual and intuitive means from the specimen rack in which the specimens are held, so that it is possible to distinguish and classify the target specimen conditions and their positions of abnormally detected specimens, without comparing, by an operator, the monitor screen of the personal computer physically remote from the unloading position and the printed-out matters of information media such as printing sheets.

As a result, not only a work efficiency of the operator is improved, but also advantages can be expected such that a possibility for an artificial mistake such as a switched specimen is reduced. Further, reliability, work efficiency and economical efficiency for the test work can be enhanced in a facility in which the pretreatment device and analyzing device are operated.

The other objects, features and advantages of the invention will become apparent from the following description of the embodiments of the invention taken in conjunction with the accompanying drawings.

DETAILED DESCRIPTION OF THE INVENTION

Hereinafter, embodiments of the invention will be described with reference to the drawings.

Figures 1, 2:
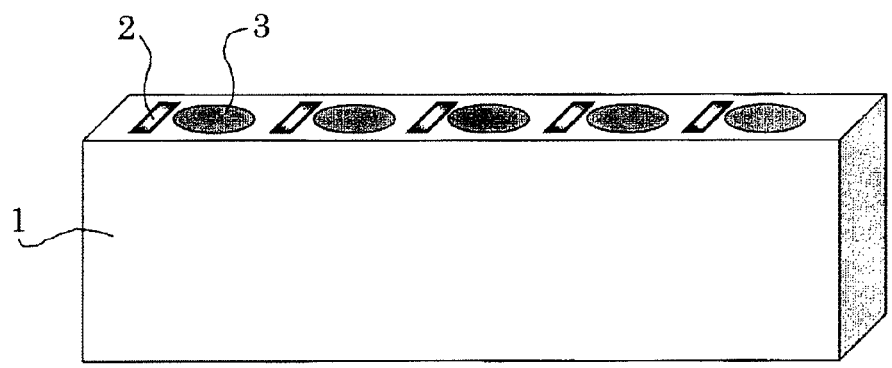
FIG. 1 is a perspective view showing a specimen rack provided by the invention.
FIG. 2 is an explanatory diagram showing an example of a notification requirement, notification contents and a notification method.

FIG. 1 is a perspective view showing a specimen rack to be provided by the invention. A specimen rack 1 is of a rectangular solid shape, and includes a specimen container loading slot 3 to hold a cylindrical shaped specimen container, a luminous body 2 (for example, LEDs (light-emitting diode), a display constituted by an organic EL or liquid crystal) corresponding to each of the specimen container loading slots 3. In the specimen rack 1 according to the embodiment, the luminous body 2 having a single color or plural colors as a notification unit is disposed in a top portion of the specimen rack 1 and at a vicinity closer to the specimen container loading slot 3 corresponding to a specimen, as an example, compared with a specimen container loading slot 3 not corresponding to the specimen. The luminous body 2 may be disposed at a position above the top portion of the specimen rack 1. Note that the top portion means an upper surface of the specimen rack 1. As the notification unit, a notification by a sound (speaker etc.) or a vibration (oscillator etc.) may be used.

FIG. 1 shows five specimen container loading slots 3 to hold five specimen containers, as held by the specimen rack 1. The number of specimen containers held by the specimen rack 1 is not limited to "five" as well as the number of specimen container loading slots 3, but may also be "one" or "ten" in the embodiment of the invention. Further, the luminous body 2 may be disposed not only between the specimen container loading slots 3 and on the vicinity of the specimen container loading slots 3, but also on any positions where an operator can visually recognize correspondence to the respective specimens. However, in the case where the luminous body 2 is disposed on a position far apart from a corresponding specimen, it is likely that a visual recognition of correspondence between a luminous body 2 and corresponding specimen container is degraded, in comparison with the case where the luminous body 2 is disposed on the vicinity of specimen container loading slot 3. Further, the luminous body 2 may also be disposed on a side surface of the specimen rack 1 (desirably, a side surface close to the top face of the specimen rack 1 among other surfaces) or in the specimen container loading slot 3 so that a luminous ray is transmitted through the side surface of the specimen rack 1.

FIG. 2 is an example of a correspondence table showing a notification requirement, notification contents, and a notification method including a color of the luminous body and a luminous mode. For example, when a sensor A for detecting a clogging pipette which sucks a specimen is actuated as on-state, as an abnormality in a treatment and analysis operation, a result of detecting the clogging pipette is notified to outside (operator, for example) by the luminous color "red" of the luminous body 2 and the luminous mode "turned ON". Similarly, when a sensor B for detecting a fluid volume shortage is actuated as on-state, the fluid volume shortage is notified to outside by the luminous color "green" of luminous body 2 and the luminous mode "blink". By using the correspondence table shown in FIG. 2, the luminous color of the luminous body 2 and luminous mode can be determined as the notification method of notification means, when sensor information meets the notification requirement. Alternatively, only the abnormality may be indicated by a single color and a single luminous mode.

Figure 3:
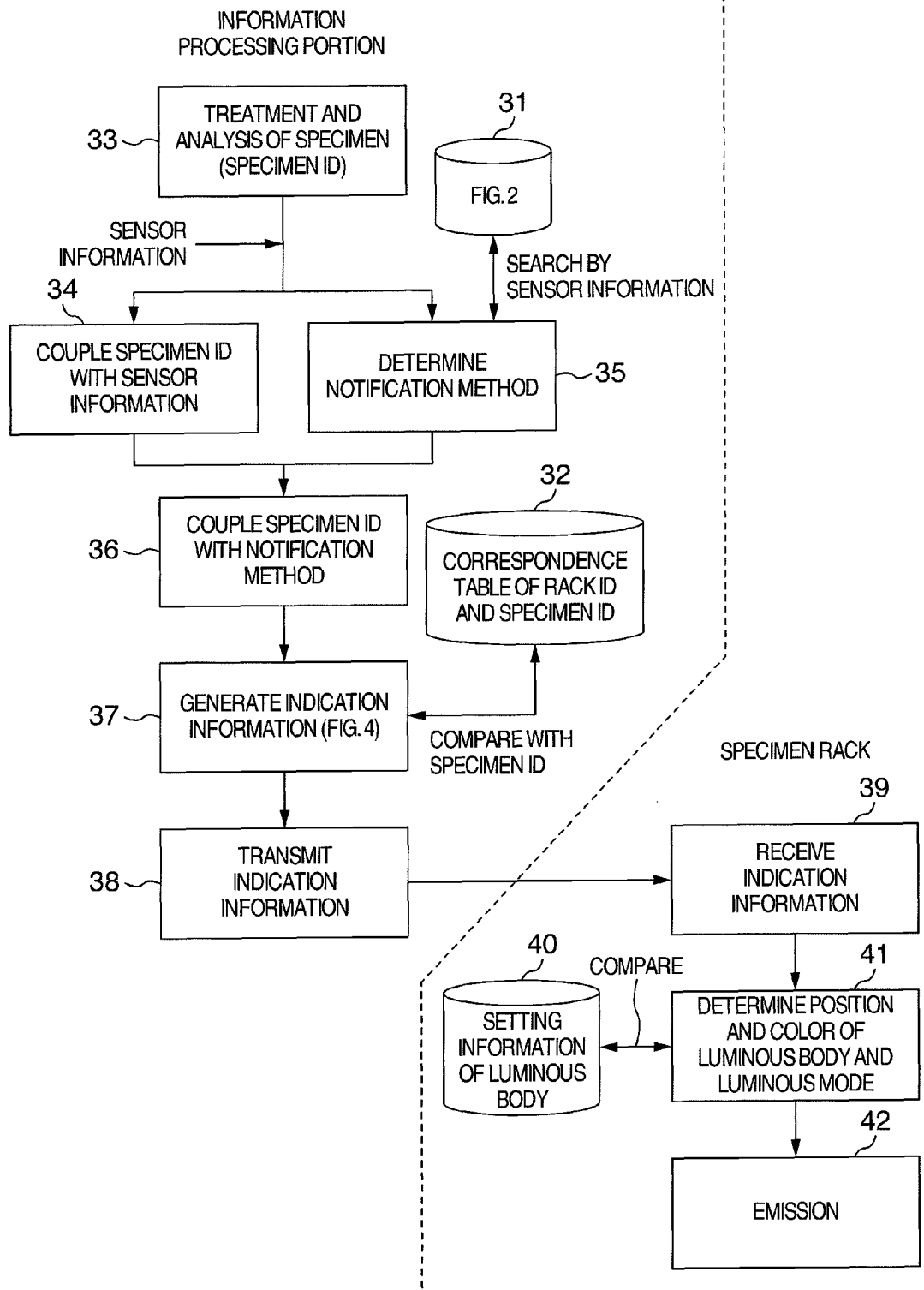
FIG. 3 is a flow chart showing steps from a treatment and analysis to a performance of a notification unit.

FIG. 3 is a flow chart showing steps from a specimen treatment and analysis to a performance of notification by the notification unit. An analyzing device and pretreatment device have an information processing portion (for example, CPU) and a storage unit for storing programs, a database and a table. The specimen rack 2 also has an information processing portion (for example, microcomputer) and a storage unit for storing programs, a database and a table.

The information processing portion in the analyzing device or pretreatment device allots a specimen ID for identifying a target specimen to be subjected to the treatment and analysis to the specimen held on the specimen container. The storage unit of the analyzing device and pretreatment device stores the correspondence table shown in FIG. 2.

The treatment and analysis are performed for the specimen having the specimen ID (step 33). When an abnormality is detected by the sensor, and the information processing portion in the analyzing device or pretreatment device receives sensor information indicating the abnormality, the information processing portion couples the sensor information to the specimen ID (step 34). For example, the specimen ID and sensor information are stored in the storage unit to correspond in one to one relation, so that the sensor information can be coupled to the specimen ID. On the other hand, the information processing portion in the analyzing device or pretreatment device uses the correspondence table shown in FIG. 2 (step 31) to search the notification method (luminous color and luminous type) on the basis of the sensor information (step 35). The information processing portion in the analyzing device or pretreatment device then couples the notification method to the specimen ID (step 36). As a result of the foregoing steps, it becomes possible to determine which notification method is to be performed for the specimen having the specimen ID.

A rack ID is also allotted to each of the specimen racks 1 in advance to identify them, and the storage unit (for example, barcode, IC chip or EEPROM) contained in the respective specimen racks 1 holds the respective rack IDs. Prior to the treatment and analysis, the information processing portion in the analyzing device or pretreatment device generates a correspondence table (step 32) indicating correspondence between rack IDs and specimen IDs such that which specimen is held on which of the specimen rack 1 and which of the specimen container loading slot 3, on the basis of ID information, such as a barcode applied to the specimen racks 1 and specimen containers, and stores the correspondence table in the storage unit of the analyzing device or pretreatment device. The information processing portion conducts collation to determine that the specimen having the specimen ID of interest is held in which of the specimen rack 1 and in which of the specimen container loading slot 3, on the basis of the correspondence table (step 32), so that the rack ID that holds the specimen of interest is identified and indication (instruction) information is then generated to indicate as to which of the luminous bodies 2 in the specimen rack 1 is turned on in which color or is to blink (step 37), and the indication information is transmitted to the specimen rack 1 (step 38).

Figures 4, 5:
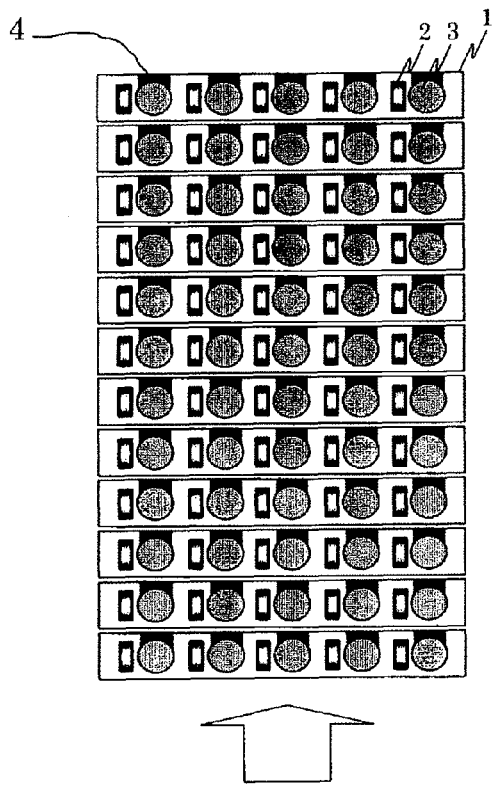
FIG. 4 is an explanatory diagram showing an example of indication information.
FIG. 5 is a plan view showing the specimen racks aligned in an unloading position.

FIG. 4 is a table showing the indication information in the case where the number of specimen container loading slots 3 on the specimen rack 1 is "five." Referring to FIG. 4, specimen IDs are associated with respective rack IDs of the specimen racks 1 and with positions of specimen container loading slots 3 of the respective specimen racks. Further, corresponding notification methods (luminous color and luminous mode) are also associated therewith.

The indication information determined by the foregoing steps is transmitted from the communication unit in the specimen carrier system to the communication unit on the specimen rack 1 (step 39). In a possible transmission method in this case, the indication information is transmitted from the communication unit in the specimen carrier system to the communication unit on the specimen rack 1 such that, when the specimen rack 1 moves from the units for performing the specimen treatment and analysis up to the unloading position in the specimen carrier system on a carrier line and upon passing through the vicinity of the communication unit in the specimen carrier system, the rack ID on the specimen rack 1 and specimen ID are read by using the respective communication units in the specimen rack and specimen carrier system so that when the passing specimen rack 1 which holds an abnormally detected specimen is recognized, the indication information is transmitted from the communication unit in the specimen carrier system to the communication unit on the specimen rack 1. Alternatively, when the maximum accommodation number of specimen racks 1 or a certain number thereof are carried at the unloading position, or the operator indicates a transmission to the specimen rack 1, the indication information is broadcasted from the communication unit provided in the unloading position to the communication units in the respective specimen racks 1 aligned in the unloading position so that the rack ID and specimen ID are compared both on the specimen carrier system side and on the specimen rack side so that the specimen rack having the corresponding ID receives the indication information. To this end, the specimen rack 1 requires that information concerning the specimen ID of the specimen held thereon and the position on the specimen rack 1 is stored temporarily in the storage unit. The information is transmitted from the communication unit in the specimen carrier system to the communication unit on the specimen rack 1. As the time period of the transmission and reception, a time period from when the ID such as barcode on the specimen rack 1 or specimen container is read to a time before the treatment and analysis are performed, is desirable. Further, it is necessary to judge correctly a transmission destination of the indication information not only by the rack ID, but also a combination with the specimen ID which does not allow the same ID basically, since it is likely that the specimen rack 1 having the same rack ID are present in plural numbers on one specimen carrier system and pretreatment device and analyzing device.

The storage unit on the specimen rack 1 stores setting information (step 40) as read-only information, in advance, concerning a number representing a position of the specimen container loading slot 3 on the specimen rack 1 and the type of luminous color to be emitted and the luminous mode, in respect of the luminous body provided on the specimen rack 1 itself. The information processing portion in the specimen rack 1 compares the setting information (step 40) with the received indication information (FIG. 4) so that the position of luminous body 2 to be emitted, luminous color and luminous mode are determined (step 41) to emit light from the luminous body 2 (step 42). After receiving the indication information, it is possible to turn the corresponding luminous body 2 on or to blink any time, on the basis of the indication information. However, it is desirable that a time period of emitting light from the luminous body 2 is from a start time to an end time for working on distinguishing the plural specimens aligned in the unloading position of the specimen rack 1 by the operator. For this reason, a start signal and an end signal may be transmitted from the analyzing unit (device) or pretreatment unit (device) to the specimen rack 1 to control the start and end of emitting the light from the luminous body 2 in accordance with an indication by the operator who operates a console or an operational screen that are part of the specimen carrier system, analyzing device and pretreatment device. Further, a sensor or switch may be provided on the specimen rack 1 or a carrier rail for carrying the specimen rack 1 or a structure near the carrier rail in advance so that it detects the specimen rack 1 arriving at a predetermined position (position where the operator works to distinguish the specimens during a time period from the start time to the end time) on the carrier rail and, using the detected signal of the sensor or switch as a trigger, the specimen rack 1 itself may control the start and end of the light emission from the luminous body 2 or, in response to the start signal and end signal transmitted to the specimen rack 1 from the analyzing unit or pretreatment unit, the specimen rack 1 may control the start and end of emitting light from the luminous body 2. An electric feeding unit (for example, supply electrode) to the specimen rack 1 may be provided on a predetermined position alone where the specimen rack 1 is present (position where the operator works to distinguish the specimens during a time period from the start time to the end time) on the carrier rail. Consequently, the specimen rack 1 receives an electric power to operate itself only when the specimen rack 1 exists at the predetermined position on the carrier rail.

In addition, the notification contents are not limited to the information, such as a clogging pipette and specimen's fluid volume shortage necessary for a distinguishing at the unloading position for use in the treatment and analysis again, that are information on the specimen condition and progress in analyzing of specimens on the treatment and analysis, detected by the sensors provided in the pretreatment device and analyzing device. As indicated by FIG. 2, it suffices that the notification requirement for performing the notification unit, the notification contents to be notified to outside and the luminous color and luminous mode of the luminous body 2 are associated with each other in advance. For example, the condition that all of the sensors on the devices are not actuated may be made the notification requirement so that the luminous body 2 may emit light to notify that the specimens are normal for which all of the necessary treatment and analysis have normally completed. For another example, the condition that information erasure is completed normally when temporarily stored information in the storage unit on the specimen rack 1 is reset may be made the notification condition so that the luminous body 2 may emit light to notify a completion of the reset. A time period for notifying that a specimen is normal is preferably, but not limited to, a time period from the start to the end of the distinguishing work by the operator for explicit distinction over a specimen that is detected by the sensors due to the clogging pipette and fluid volume shortage. Further, the notification indicating the completion of reset may possibly be made by emitting the luminous body for a certain emission time period from a time point of erasing the information from the storage unit in the specimen rack 1 by the operator.

FIG. 5 is an explanatory diagram showing that the specimen racks 1 in FIG. 1 are aligned in lateral direction perpendicular to a visual line of the operator in the unloading position of the specimen racks 1. Referring to FIG. 5, there are 12 consecutive specimen racks 1, each of which can hold five specimen containers. The luminous body 2 is disposed on the left side of specimen container loading slot 3 in relation to the visual line direction of the operator. The luminous body 2 may be disposed on a location where the operator can recognize visually, for example, the right side of specimen container loading slot 3 or near side to the operator in relation to the visual line direction of the operator, except for a portion 4 which is hidden behind the specimen container in relation to the visual line direction of the operator.

In a housing or reposition method shown in FIG. 5, the luminous body 2 is not hidden behind the adjacent specimen rack 1 and the specimen container, in the case of the luminous body 2 disposed as shown in FIG. 1. Therefore, the operator can easily recognize the emission of luminous body 2 and identify a corresponding relation between the luminous body 2 and the specimen. In this way, an optimum requirement for the location where the luminous body 2 is disposed on the specimen rack 1 is such that, taking into account of a position or posture of the specimen rack 1 and a direction of the specimen rack 1 in relation to the visual direction of the operator at the time of luminous emission, and the state of overlapping with adjacent specimen racks 1, specimen containers and a casing portion of the specimen carrier system, it is desirable that the luminous emission of the luminous body 2 can be recognized and a correspondence relation between the luminous body 2 and specimen can be identified without being hampered.

In the embodiment of the invention, the unloading position may be either separated from the input portion or the same position thereof, depending on the constitution of the specimen carrier system, analyzing device and pretreatment device.

Under the foregoing requirements, a luminous body constituted of a combination of a plural colors is correspondingly disposed on each of the specimens, so that notification information amount can be increased by the number of color combinations. For example, the combination of 4×4=16 kinds can be notified as the notification information amount if a luminous body having four colors is combined by two. Further, the combined color luminous body 2 is turned on or to blink alternately, so that the notification information amount can be increased. However, depending on a combination of luminous colors, it may become difficult to distinguish each of the same combined colors, undesirably going against the intention according to the present invention of providing the visual and intuitive notification unit. Therefore, the combination of luminous colors should be considered taking the foregoing possibility into account.

Figure 6:
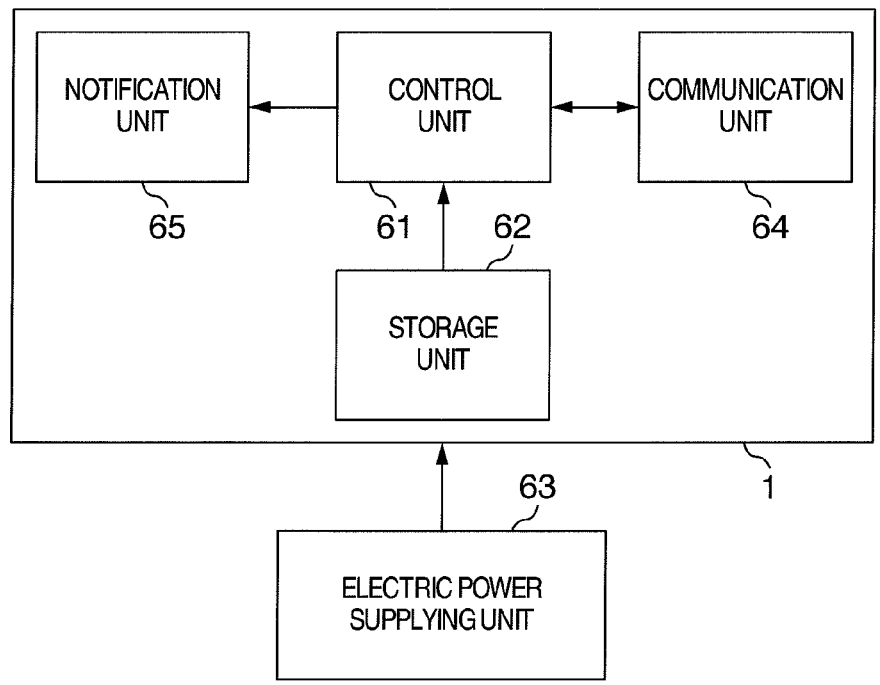
FIG. 6 is a block diagram showing units to be mounted on the specimen rack.

FIG. 6 is a block diagram showing the specimen rack 1 constituted by a notification unit 65 and a communication unit 64 and a control unit 61 and a storage unit 62 for executing the operation of the notification unit 65 and communication unit 64. The specimen rack 1 receives an electric power from a power supply unit 63.

The control unit 61 makes a correspondence relation of a specimen ID, a position of the luminous body 2, a luminous color and a luminous emission mode, contained in the indication information, and emits light from the luminous body 2 specified by the rack ID and the position of specimen container loading slot 3 in accordance with the correspondence relation to control the notification unit 65, on the basis of the indication information (FIG. 4, for example) obtained from outside (for example, analyzing device or pretreatment device) through the communication unit 64 and programs stored in the storage unit 62. Information to be temporarily saved is stored in the storage unit 62, among pieces of information obtained from outside. The storage unit 62 may be used desirably of an existing storage unit in response to information contents to be stored and an application form, for example, a ROM (Read Only Memory) used for information unnecessary for a rewriting such as a control program, and a RAM (Random Access Memory) used for saving information necessary for a sequential rewriting such that which of a luminous body 2 on the specimen rack 1 is emitted by what a color of emission, and for temporarily saving information, etc.

The temporarily stored information in the RAM can be made disappeared upon cutting off of the power supply to the specimen rack 1 (particularly, storage unit). Alternatively, the temporarily stored information can be deleted sequentially in response to an instruction from the operation of the console, the button on the operational screen, and the switch, provided in the pretreatment device and analyzing device, or the operation of an information processing device such as a personal computer communicating with the pretreatment device and analyzing device, by using communication units provided in the specimen rack 1 and specimen carrier system or the temporarily stored information can be deleted by conducting an operation for information deletion such that a reset button provided on the specimen rack 1 is depressed. Alternatively, the temporarily stored information may also be deleted arbitrarily and automatically in accordance with a predetermined requirement and a predetermined logic in the specimen carrier system, analyzing device and pretreatment device, or a specimen rack installing facility independent from the foregoing system and units (devices), without instruction from the operator.

The electric power necessary for performing the foregoing units such as the notification unit 65 and communication unit 64 is supplied from the power supply unit 63. In this regard, in the case where the communication unit 64 is constituted of an ID tag such as a RFID (Radio Frequency Identification) having a built-in rectifier circuit, the power supply unit 63 may not be required to supply the electric power to the communication unit 64. Further, when the notification unit 65 is constituted of a LED-integrated type RFID including the control unit 61, storage unit 62 and communication unit 64, connected with the communication unit 65 and by adapting the LED-integrated type RFID to be controlled by the analyzing device or pretreatment device in such a way that the LED emits light when a RFID-destination signal is received only from the analyzing device or pretreatment device, it becomes not necessary to provide wiring among the control unit, storage unit and power supply unit 63, other than the LED-integrated type RFID. It is then desirable that the foregoing units are fabricated in the specimen rack 1 in a certain size and shape which are allowed to downsize the specimen rack 1, because of little mounting space for the pretreatment device and analyzing device to which the specimen rack 1 are carried, and the input portion, the carrier rail and the unloading position in the specimen carrier system. For example, as shown in FIG. 1, using the LED capable of emitting light by a small size and low electric power to the notification unit 65 enables not only the notification unit 65 to make downsized, but also the power supply portion to make downsized, therefore, the specimen rack 1 provided by the invention is used preferably for the pretreatment and analysis.

Figure 7:
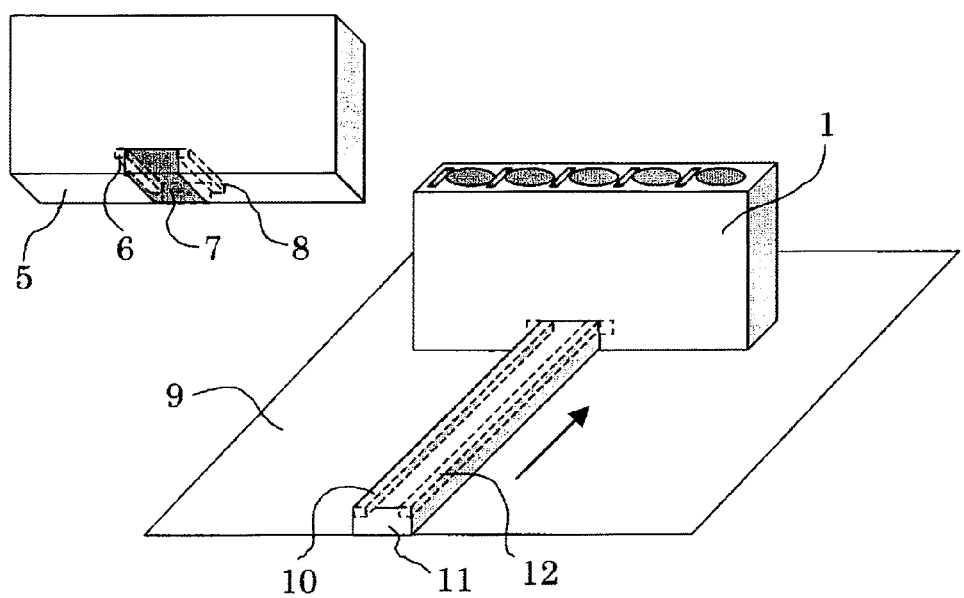
FIG. 7 is perspective views showing an example of a power receiving and supplying unit mounted on the specimen rack and specimen carrier system.

FIG. 7 is a view showing an embodiment of the power supply unit 63 in connection with the specimen rack 1 and housing (repository) portion 9. Electric power is supplied from the specimen carrier system to the specimen rack 1 in a contact manner. Supplying electrodes 10, 12 are formed on a carrier rail 11 (or a specimen rack installing rail) which is disposed on the unloading position 9 (or input portion or specimen rack installing facility) for the purpose of safety against overturning and fixing a movement route for the specimen rack 1 in the unloading position 9. Receiving electrodes 6, 8 are formed in a groove portion 7 on a bottom surface 5. The groove portion 7 is disposed in the bottom surface 5 of the specimen rack 1 so that the specimen rack 1 carried on the carrier rail 11 can move in the unloading position 9.

The receiving electrodes 6 and 8 in the groove 7 of the specimen rack 1 are so disposed that they correspond to the supplying electrodes 10 and 12 on the carrier rail 11 of the specimen carrier system, respectively. The specimen rack 1 may have an accumulator unit (not shown) for accumulating electric power supplied from the specimen carrier system or a battery charger (not shown). In the case where the accumulator unit is not used for receiving electric power the electric power and supplying it to the notification unit 65 and communication unit 64 in the specimen rack 1, it is necessary to provide a dry battery or fuel battery as a power source in the specimen rack 1 to supply electric power to the notification unit 65 and communication unit 64.

In the case where the unloading position 9 shown in FIG. 7 is removable from the main body of specimen carrier system, a communication unit used for communicating the information necessary for the control and a power receiving and supplying unit for performing the notification unit provided in the specimen rack 1 may be provided in the move destination, or the main body of specimen carrier system is provided in the move destination, as required, so that similar advantages can be obtained from the condition either before or after the unloading position 9 is removed, even though the move destination after moved the unloading position 9 is independent from the specimen carrier system.

Further, even in the case where the specimen rack 1 is placed separately in the specimen rack installing facility independent from the specimen carrier system, analyzing device, or pretreatment device, the unit used for communicating information necessary for the control and the power receiving and supplying unit for performing the notification unit provided in the specimen rack 1 are provided for the specimen rack installing facility, specimen rack 1, or the main body of specimen carrier system, similarly to the foregoing removable unloading position 9 from the specimen carrier system, so that the foregoing similar advantages can be obtained from the condition either before or after the unloading position 9 is removed.

Figure 8:
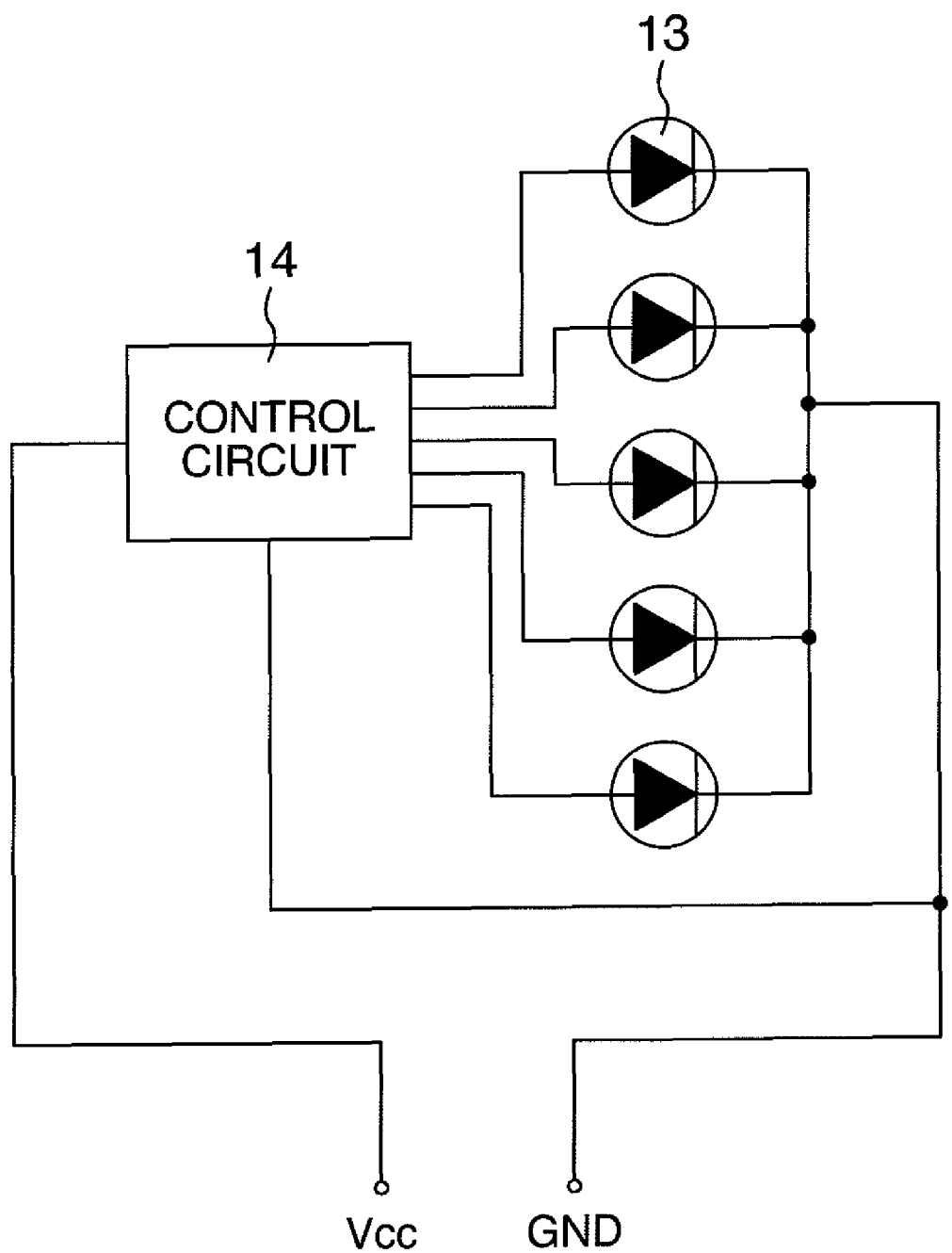
FIG. 8 is a circuit diagram showing an example of a wiring from the power receiving and supplying unit to a notification unit.

FIG. 8 is a circuit diagram showing the notification unit 65 using LEDs 13, in which the notification unit 65 is connected with the receiving electrodes 6, 8 formed with the groove portion 7 on the specimen rack 1 as shown in FIG. 7. A control circuit 14 contains a resistor and capacitor used for a current regulation relative to the LEDs 13, and also contains a microcomputer corresponding to the control unit 61. The circuit shown in FIG. 8 corresponds to using five LEDs 13 corresponding to the five specimen container loading slots 3. A plurality of LEDs 13 may be corresponded to each of the specimen container loading slots 3, and the power supply unit to the LEDs 13 may be replaced with other types.

The specimen rack and specimen carrier system provided by the invention are used in hospitals, inspection centers, specimen laboratories, etc., where a number of specimens are handled, to provide requirements for reliability of the analysis and treatment operations, high throughput, low cost, etc. Competitors have developed and sold the specimen rack and specimen carrier system. The LED described in the embodiment as the notification unit of the specimen rack 1 can be mounted on the presently and widely available specimen rack having a certain size, and produced by the competitors because such LED can emit light by a small size and low power consumption. Further, it is possible to select colors corresponding to the notification contents because there are plural colors (red, yellow, blue, green and white). It is also possible to produce the specimen rack and specimen carrier system in mass production, low price, and long life, which is one of advantages. On the other hand, the communication unit used for the specimen rack and specimen carrier system has advanced in low cost and high technology with an ID tag such as information readable and writable RFID by a radio wave, therefore, the increase of employing the RFID is promised in place of the barcode which is presently and widely used as an ID to be applied to the specimen rack 1. It is thus possible to promise use of products developed by the present invention.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A specimen rack configured to hold at least one specimen container, each specimen container configured to contain a specimen, the specimen rack comprising:
 a luminous body disposed in or above an upper surface of the specimen rack, and configured to notify information detected by a sensor to outside the specimen rack by emitting a color selected from a set of colors and an emission mode selected from a set of emission modes, the information concerning a specimen contained in the at least one specimen container held on a specimen rack, the information including a status of progress in analyzing a specimen and/or a specimen condition;
 a communication unit configured to transmit information to and receive information from outside the specimen rack, the information being necessary for the luminous body;
 wherein the specimen rack is configured to be removable from a specimen carrier system at an input position or an unloading position of the specimen carrier system, the specimen rack including at least one of:
 (1) the communication unit being further configured to communicate in a wired or wireless manner with a communication unit provided in the specimen carrier system, or with a communication unit that is provided separately from the specimen carrier system and that is adapted to mount therein an input position and an unloading position after being removed from the specimen carrier system, and
 (2) a unit configured to receive electric power in a wired or wireless manner from the specimen carrier system, or to receive electric power from an electric power supplying unit that is provided separately from the specimen carrier system and that is adapted to mount therein the input position and unloading position after being removed from the specimen carrier system.

2. A specimen rack configured to hold at least one specimen container, each specimen container configured to contain a specimen, the specimen rack comprising:
 a luminous body disposed in a vicinity of a specimen container loading slot corresponding to the specimen, and configured to notify information detected by a sensor to outside the specimen rack by emitting a color selected from a set of colors and an emission mode selected from a set of emission modes, the information concerning a specimen contained in the at least one specimen container held on a specimen rack, the information including a status of progress in analyzing a specimen and/or a specimen condition;
 a communication unit configured to transmit information to and receive information from outside the specimen rack, the information being necessary for the luminous body;
 wherein the specimen rack is configured to be removable from a specimen carrier system at an input position or an unloading position of the specimen carrier system, the specimen rack including at least one of:
 (1) the communication unit being further configured to communicate in a wired or wireless manner with a communication unit provided in the specimen carrier system, or with a communication unit that is provided separately from the specimen carrier system and that is adapted to mount therein an input position and an unloading position after being removed from the specimen carrier system, and
 (2) a unit configured to receive electric power in a wired or wireless manner from the specimen carrier system, or to receive electric power from an electric power supplying unit that is provided separately from the specimen carrier system and that is adapted to mount therein the input position and unloading position after being removed from the specimen carrier system.

3. A specimen rack configured to hold at least one specimen container, each specimen container configured to contain a specimen, the specimen rack comprising:
- a luminous body configured to notify information detected by a sensor to outside the specimen rack by emitting a color selected from a set of colors and an emission mode selected from a set of emission modes, the information concerning a specimen contained in the at least one specimen container held on a specimen rack, the information including a status of progress in analyzing a specimen and/or a specimen condition, wherein at least one of said color and/or emission mode are associated in advance with said analyzing status, progress in analyzing a specimen, and/or the specimen condition for the specimen;
- a communication unit configured to transmit information to and receive information from outside the specimen rack, the information being necessary for the luminous body;
- wherein the specimen rack is configured to be removable from a specimen carrier system at an input position or an unloading position of the specimen carrier system, the specimen rack including at least one of:
  - (1) the communication unit being further configured to communicate in a wired or wireless manner with a communication unit provided in the specimen carrier system, or with a communication unit that is provided separately from the specimen carrier system and that is adapted to mount therein an input position and an unloading position after being removed from the specimen carrier system, and
  - (2) a unit configured to receive electric power in a wired or wireless manner from the specimen carrier system, or to receive electric power from an electric power supplying unit that is provided separately from the specimen carrier system and that is adapted to mount therein the input position and unloading position after being removed from the specimen carrier system.

4. A specimen carrier system, comprising:
- a specimen analyzing device and/or a specimen analyzing pretreatment device having a monitor screen configured to display a status of progress in analyzing each of a plurality of specimens; and
- a plurality of specimen racks, each configured to hold at least one specimen container, each specimen container configured to contain a specimen, the specimen rack including:
  - a luminous body disposed in a vicinity of a specimen container loading slot corresponding to the specimen, and configured to notify information detected by a sensor to outside the specimen rack by emitting a color selected from a set of colors and an emission mode selected from a set of emission modes, the information concerning a specimen contained in the at least one specimen container held on a specimen rack, the information including a status of progress in analyzing a specimen and/or a specimen condition;
  - a communication unit configured to transmit information to and receive information from outside the specimen rack, the information being necessary for the luminous body;
  - wherein the specimen rack is configured to be removable from a specimen carrier system at an input position or an unloading position of the specimen carrier system, the specimen rack including at least one of:
    - (1) the communication unit being further configured to communicate in a wired or wireless manner with a communication unit provided in the specimen carrier system, or with a communication unit that is provided separately from the specimen carrier system and that is adapted to mount therein an input position and an unloading position after being removed from the specimen carrier system, and
    - (2) a unit configured to receive electric power in a wired or wireless manner from the specimen carrier system, or to receive electric power from an electric power supplying unit that is provided separately from the specimen carrier system and that is adapted to mount therein the input position and unloading position after being removed from the specimen carrier system.

5. The specimen carrier system according to claim 4, further comprising a communication unit configured to transmit and receive information to and from a specimen rack in a contact or non-contact manner, wherein
- the communication unit is disposed on a carrier line provided from an input position up to the specimen analyzing pretreatment device or the specimen analyzing device and/or a carrier line provided from the specimen analyzing pretreatment device or the specimen analyzing device up to an unloading position.

6. A specimen carrier system, comprising:
- a specimen carrier system according to claim 4;
- a carrier device configured to carry the plurality of specimen racks;
- wherein the monitor screen is configured to display either a normality or an abnormality of the specimen contained in the specimen container, or the normality or the abnormality of the an analyzing treatment for the specimen contained in the specimen container, when a specimen rack is present at a position on a carrier device where the specimen is tested by an operator.

7. A specimen carrier system that includes a specimen rack configured to hold at least one specimen container, each specimen container configured to contain a specimen, the specimen rack comprising:
- a luminous body configured to notify information detected by a sensor to outside the specimen rack by emitting a color selected from a set of colors and an emission mode selected from a set of emission modes, the information concerning a status of progress in analyzing a specimen, and/or a specimen condition of a specimen contained in the at least one specimen container, and the luminous body being disposed in a vicinity of a specimen container loading slot corresponding to the specimen;
- a communication unit configured to transmit information to and receive information from outside the specimen rack, the information being necessary for the luminous body;
- wherein the specimen rack is configured to be removable from the specimen carrier system at an input position or an unloading position of the specimen carrier system, the specimen rack including at least one of:
  - (1) the communication unit being further configured to communicate in a wired or wireless manner with a communication unit provided in the specimen carrier system, or with a communication unit that is provided separately from the specimen carrier system and that is adapted to mount therein an input position and an unloading position after being removed from the specimen carrier system, and
  - (2) a unit configured to receive electric power in a wired or wireless manner from the specimen carrier system, or to receive electric power from an electric power supplying unit that is provided separately from the specimen carrier system and that is adapted to mount therein the input position and unloading position after being removed from the specimen carrier system.

8. The specimen carrier system according to claim 4,
wherein said specimen rack comprises a luminous body for each specimen container; and
wherein said luminous body and a display of a corresponding specimen on the monitor screen emit light of a corresponding color.

9. The specimen carrier system according to claim 8, further comprising a communication unit configured to transmit and receive information to and from a specimen rack in a contact or non-contact manner, wherein
the communication unit is disposed on a carrier line provided from an input position up to the specimen analyzing pretreatment device or the specimen analyzing device and/or a carrier line provided from the specimen analyzing pretreatment device or the specimen analyzing device up to an unloading position.

10. A specimen carrier system, comprising:
a specimen rack system according to claim 8;
a carrier device configured to carry the specimen rack;
wherein the monitor screen is configured to display either a normality or an abnormality of the specimen contained in the specimen container, or the normality or the abnormality of the an analyzing treatment for the specimen contained in the specimen container, when a specimen rack is present at a position on a carrier device where the specimen is tested by an operator.

11. The specimen rack system according to claim 4, wherein a specimen rack includes at least: (2) the unit configured to receive electric power in the wired or wireless manner from the specimen carrier system, or to receive electric power from the electric power supplying unit that is provided separately from the specimen carrier system; and
wherein the electric power supplying unit is adapted to be mounted in any of: (a) the input position, (b) an unloading position after being removed from the specimen carrier system, and (c) a move destination.

12. The specimen rack of claim 1,
wherein a sensor is provided in a pretreatment device configured to perform pretreatment for specimen analysis, and/or is provided in an analyzing device configured to perform specimen analysis.

13. The specimen rack of claim 2,
wherein a sensor is provided in a pretreatment device configured to perform pretreatment for specimen analysis, and/or is provided in an analyzing device configured to perform specimen analysis.

14. The specimen rack of claim 3,
wherein a sensor is provided in a pretreatment device configured to perform pretreatment for specimen analysis, and/or is provided in an analyzing device configured to perform specimen analysis.

15. The specimen carrier system of claim 4,
wherein a sensor is provided in a pretreatment device configured to perform pretreatment for specimen analysis, and/or is provided in an analyzing device configured to perform specimen analysis.

16. The specimen carrier system of claim 7,
wherein a sensor is provided in a pretreatment device configured to perform pretreatment for specimen analysis, and/or is provided in an analyzing device configured to perform specimen analysis.

17. The specimen rack of claim 1,
wherein the luminous body includes at least one of: an organic electroluminescent (EL) display, and a liquid crystal display (LCD).

18. The specimen rack of claim 2,
wherein the luminous body includes at least one of: an organic electroluminescent (EL) display, and a liquid crystal display (LCD).

19. The specimen rack of claim 3,
wherein the luminous body includes at least one of: an organic electroluminescent (EL) display, and a liquid crystal display (LCD).

20. The specimen carrier system of claim 4,
wherein the luminous body includes at least one of: an organic electroluminescent (EL) display, and a liquid crystal display (LCD).

21. The specimen carrier system of claim 7,
wherein the luminous body includes at least one of: an organic electroluminescent (EL) display, and a liquid crystal display (LCD).

* * * * *